United States Patent
Dye (10) Patent No.: US 8,506,636 B2
(45) Date of Patent: Aug. 13, 2013

(54) OFFSET RADIUS LORDOSIS

(75) Inventor: Justin Dye, Mansfield, MA (US)

(73) Assignee: Theken Spine, LLC, Akron, OH (US)

( * ) Notice: Subject to any disclaimer, the term of this patent is extended or adjusted under 35 U.S.C. 154(b) by 341 days.

(21) Appl. No.: 11/767,868

(22) Filed: Jun. 25, 2007

(65) Prior Publication Data

US 2008/0065219 A1 Mar. 13, 2008

Related U.S. Application Data (60) Provisional application No. 60/825,089, filed on Sep. 8, 2006, provisional application No. 60/825,084, filed on Sep. 8, 2006.

(51) Int. Cl.
*A61F 2/44* (2006.01)
(52) U.S. Cl.
USPC .................................. 623/17.16; 623/17.11
(58) Field of Classification Search
USPC ................... 623/17.12, 17.15, 17.16
See application file for complete search history.

(56) References Cited

U.S. PATENT DOCUMENTS

| 43,994 | A | 8/1864 | Myers |
|---|---|---|---|
| 204,596 | A | 6/1878 | Nicholson |
| 354,616 | A | 12/1886 | Alexander |
| 472,259 | A | 4/1892 | Goodell et al. |
| 905,132 | A | 1/1908 | Bacon |
| 1,151,197 | A | 8/1915 | Lang |
| 1,538,032 | A | 5/1925 | Fischer |
| 2,388,920 | A | 11/1945 | Jayne |
| 2,455,064 | A | 11/1948 | Johnson |
| 2,485,389 | A | 10/1949 | LaClair |
| 2,677,369 | A | 3/1952 | Knowles |
| 2,816,351 | A | 12/1957 | Sauers |
| 3,030,947 | A | 4/1962 | Engelbert |
| 3,136,040 | A | 6/1964 | Bauer |
| 3,486,505 | A | 12/1969 | Morrison |
| 3,529,497 | A | 9/1970 | Brook |
| 3,585,994 | A | 6/1971 | Huggler et al. |
| 3,626,935 | A | 12/1971 | Pollock |
| 3,848,601 | A | 11/1974 | Ma et al. |
| 3,867,728 | A | 2/1975 | Stubstad et al. |
| 4,023,559 | A | 5/1977 | Gaskell |

(Continued)

FOREIGN PATENT DOCUMENTS

| DE | 19710392 | 7/1999 |
|---|---|---|
| EP | 1157676 | 11/2001 |

(Continued)

*Primary Examiner* — Nicholas Woodall
*Assistant Examiner* — Christine Nelson
(74) *Attorney, Agent, or Firm* — Middleton Reutlinger; Robert H. Eichenberger; Chad D. Bruggeman (57) ABSTRACT

A vertebral body replacement or spacer that re-creates a lordosis angle (or other angle) of a human spine. An embodiment of the spacer may comprise contoured superior and inferior bearing surfaces. More particularly, the contoured surfaces may be defined by compound curves such as two radii substantially orthogonal to each other. As a result, the bearing surfaces may conform to the convex end plates of adjacent vertebra. In another embodiment, the present invention may provide a method of establishing a lordosis angle. The method may comprise inserting a spacer into an intervertebral space and positioning the spacer in such a manner that the contoured surfaces generally correspond to the end plates of the adjacent vertebra. However, the spacers and methods of the embodiments of the present invention may be used to re-create other angles in the human spine.

24 Claims, 9 Drawing Sheets

(56) References Cited

U.S. PATENT DOCUMENTS

| | | |
|---|---|---|
| 4,309,777 A | 1/1982 | Patil |
| 4,349,921 A | 9/1982 | Kuntz |
| 4,423,721 A | 1/1984 | Otte et al. |
| 4,501,269 A | 2/1985 | Bagby |
| 4,553,273 A | 11/1985 | Wu |
| 4,599,086 A | 7/1986 | Doty |
| 4,616,635 A | 10/1986 | Caspar et al. |
| 4,625,725 A | 12/1986 | Davison et al. |
| 4,714,469 A | 12/1987 | Kenna |
| 4,714,494 A | 12/1987 | Eckert |
| 4,743,256 A | 5/1988 | Brantigan |
| 4,759,766 A | 7/1988 | Buettner-Janz et al. |
| 4,790,303 A | 12/1988 | Steffee |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,904,260 A | 2/1990 | Ray et al. |
| 4,904,261 A | 2/1990 | Dove et al. |
| 4,919,153 A | 4/1990 | Chin |
| 4,993,410 A | 2/1991 | Kimsey |
| 4,997,432 A | 3/1991 | Keller |
| 5,059,193 A | 10/1991 | Kuslich |
| 5,108,402 A | 4/1992 | Chin |
| 5,171,278 A | 12/1992 | Pisharodi |
| 5,192,327 A | 3/1993 | Brantigan |
| 5,250,055 A | 10/1993 | Moore et al. |
| 5,290,312 A | 3/1994 | Kojimoto et al. |
| 5,342,365 A | 8/1994 | Waldman |
| 5,390,683 A | 2/1995 | Pisharodi |
| 5,405,391 A | 4/1995 | Hednerson et al. |
| 5,425,777 A | 6/1995 | Sarkisian et al. |
| 5,433,739 A | 7/1995 | Sluijter et al. |
| 5,439,463 A | 8/1995 | Lin |
| 5,476,467 A | 12/1995 | Benoist |
| 5,484,437 A | 1/1996 | Michelson |
| 5,496,345 A | 3/1996 | Kieturakis et al. |
| 5,522,899 A | 6/1996 | Michelson |
| 5,549,679 A | 8/1996 | Kuslich |
| 5,554,191 A | 9/1996 | Lahille et al. |
| 5,562,736 A | 10/1996 | Ray et al. |
| 5,584,831 A | 12/1996 | McKay |
| 5,586,842 A | 12/1996 | Bae et al. |
| 5,601,561 A | 2/1997 | Terry et al. |
| 5,609,635 A | 3/1997 | Michelson |
| 5,609,636 A | 3/1997 | Kohrs et al. |
| 5,645,597 A | 7/1997 | Krapiva |
| 5,653,762 A | 8/1997 | Pisharodi |
| 5,653,763 A | 8/1997 | Errico et al. |
| 5,665,122 A | 9/1997 | Kambin |
| 5,693,100 A | 12/1997 | Pisharodi |
| 5,697,977 A | 12/1997 | Pisharodi |
| 5,702,449 A | 12/1997 | McKay |
| 5,713,899 A | 2/1998 | Marnay et al. |
| 5,716,415 A | 2/1998 | Steffee |
| 5,716,416 A | 2/1998 | Lin |
| 5,720,746 A | 2/1998 | Soubeiran |
| 5,741,253 A | 4/1998 | Michelson |
| 5,749,916 A | 5/1998 | Richelsoph |
| 5,752,970 A | 5/1998 | Yoon |
| 5,776,196 A | 7/1998 | Matsuzaki et al. |
| 5,776,199 A | 7/1998 | Michelson |
| 5,782,830 A | 7/1998 | Farris |
| 5,797,909 A | 8/1998 | Michelson |
| 5,800,550 A | 9/1998 | Sertich |
| 5,860,973 A | 1/1999 | Michelson |
| 5,861,041 A | 1/1999 | Tienboon |
| 5,879,353 A | 3/1999 | Terry |
| 5,885,299 A | 3/1999 | Winslow et al. |
| 5,888,223 A | 3/1999 | Bray |
| 5,888,228 A | 3/1999 | Knothe et al. |
| 5,913,860 A | 6/1999 | Scholl |
| 5,954,635 A | 9/1999 | Foley et al. |
| 5,980,522 A | 11/1999 | Koros et al. |
| 6,033,405 A | 3/2000 | Winslow et al. |
| 6,039,761 A | 3/2000 | Li et al. |
| 6,039,762 A | 3/2000 | McKay |
| 6,059,790 A | 5/2000 | Sand et al. |
| 6,066,174 A | 5/2000 | Farris |
| 6,066,175 A | 5/2000 | Henderson et al. |
| 6,074,423 A | 6/2000 | Lawson |
| 6,080,155 A | 6/2000 | Michelson |
| 6,093,038 A | 7/2000 | Chen et al. |
| 6,093,205 A | 7/2000 | McLeod et al. |
| 6,093,207 A | 7/2000 | Pisharodi |
| 6,096,038 A | 8/2000 | Michelson |
| 6,106,557 A | 8/2000 | Robioneck et al. |
| 6,113,602 A | 9/2000 | Sand |
| 6,123,705 A | 9/2000 | Michelson |
| 6,126,689 A | 10/2000 | Brett |
| 6,136,001 A | 10/2000 | Michelson |
| 6,136,031 A | 10/2000 | Middleton |
| 6,143,032 A | 11/2000 | Schafer et al. |
| 6,156,037 A | 12/2000 | Lehuec et al. |
| 6,159,211 A | 12/2000 | Boriani et al. |
| 6,159,244 A | 12/2000 | Suddaby |
| 6,159,245 A | 12/2000 | Meriwether et al. |
| 6,162,170 A | 12/2000 | Foley et al. |
| 6,174,334 B1 | 1/2001 | Suddaby |
| 6,183,517 B1 | 2/2001 | Suddaby |
| 6,193,757 B1 | 2/2001 | Foley et al. |
| 6,206,923 B1 | 3/2001 | Boyd et al. |
| 6,206,924 B1 | 3/2001 | Timm |
| 6,214,050 B1 | 4/2001 | Huene |
| 6,235,059 B1 | 5/2001 | Benezech et al. |
| 6,245,108 B1 | 6/2001 | Biscup |
| 6,248,110 B1 | 6/2001 | Reiley et al. |
| 6,251,140 B1 | 6/2001 | Marino et al. |
| 6,261,586 B1 | 7/2001 | McKay |
| 6,264,656 B1 | 7/2001 | Michelson |
| 6,267,763 B1 | 7/2001 | Castro |
| 6,270,498 B1 | 8/2001 | Michelson |
| 6,277,120 B1 | 8/2001 | Lawson |
| 6,283,966 B1 | 9/2001 | Houfburg |
| 6,319,257 B1 | 11/2001 | Carignan et al. |
| 6,328,738 B1 | 12/2001 | Suddaby |
| 6,332,894 B1 | 12/2001 | Stalcup et al. |
| 6,368,325 B1 | 4/2002 | McKinley et al. |
| 6,368,326 B1 | 4/2002 | Dakin et al. |
| 6,368,351 B1 | 4/2002 | Glenn et al. |
| 6,371,990 B1 | 4/2002 | Ferree |
| 6,387,130 B1 | 5/2002 | Stone et al. |
| 6,395,031 B1 | 5/2002 | Foley et al. |
| 6,402,750 B1 | 6/2002 | Atkinson et al. |
| 6,419,704 B1 | 7/2002 | Ferree |
| 6,425,919 B1 | 7/2002 | Lambrecht |
| 6,436,098 B1 | 8/2002 | Michelson |
| 6,436,101 B1 | 8/2002 | Hamada |
| 6,440,142 B1 | 8/2002 | Ralph et al. |
| 6,443,990 B1 | 9/2002 | Aebi et al. |
| 6,447,543 B1 | 9/2002 | Studer et al. |
| 6,447,547 B1 | 9/2002 | Michelson |
| 6,451,019 B1 | 9/2002 | Zucherman et al. |
| 6,468,311 B2 | 10/2002 | Boyd et al. |
| 6,478,823 B1 | 11/2002 | Michelson |
| 6,482,235 B1 | 11/2002 | Lambrecht |
| 6,485,517 B1 | 11/2002 | Michelson |
| 6,488,710 B2 | 12/2002 | Besselink |
| 6,491,695 B1 | 12/2002 | Roggenbuck |
| 6,491,724 B1 | 12/2002 | Ferree |
| 6,500,205 B1 | 12/2002 | Michelson |
| 6,508,839 B1 | 1/2003 | Lambrecht et al. |
| 6,511,484 B2 | 1/2003 | Torode et al. |
| 6,511,498 B1 | 1/2003 | Fumex |
| 6,520,967 B1 | 2/2003 | Cauthen |
| 6,533,791 B1 | 3/2003 | Betz et al. |
| 6,537,280 B2 | 3/2003 | Dinger et al. |
| 6,551,320 B2 | 4/2003 | Lieberman |
| 6,558,423 B1 | 5/2003 | Michelson |
| 6,558,424 B2 | 5/2003 | Thalgott |
| 6,562,072 B1 | 5/2003 | Fuss et al. |
| 6,565,568 B1 | 5/2003 | Rogozinski |
| 6,569,201 B2 | 5/2003 | Moumene et al. |
| 6,575,978 B2 | 6/2003 | Peterson et al. |

| Patent | Date | Inventor |
|---|---|---|
| 6,592,586 B1 | 7/2003 | Michelson |
| 6,592,625 B2 | 7/2003 | Cauthen |
| 6,595,995 B2 | 7/2003 | Zdeblick et al. |
| 6,599,291 B1 | 7/2003 | Foley et al. |
| 6,599,294 B2 | 7/2003 | Fuss et al. |
| 6,602,291 B1 | 8/2003 | Ray |
| 6,610,064 B1 | 8/2003 | Goble et al. |
| 6,610,089 B1 | 8/2003 | Liu et al. |
| 6,613,089 B1 | 9/2003 | Estes et al. |
| 6,613,090 B2 | 9/2003 | Fuss et al. |
| 6,620,196 B1 | 9/2003 | Trieu |
| 6,632,247 B2 | 10/2003 | Boyer et al. |
| 6,635,060 B2 | 10/2003 | Hanson et al. |
| 6,645,211 B2 | 11/2003 | Magana |
| 6,652,533 B2 | 11/2003 | O'Neil |
| 6,656,178 B1 | 12/2003 | Veldhuizen et al. |
| 6,666,866 B2 | 12/2003 | Martz et al. |
| 6,666,889 B1 | 12/2003 | Commarmond |
| 6,676,703 B2 | 1/2004 | Biscup |
| 6,685,695 B2 | 2/2004 | Ferree |
| 6,689,167 B2 | 2/2004 | Bagby |
| 6,699,288 B2 | 3/2004 | Moret |
| 6,709,439 B2 | 3/2004 | Rogers |
| 6,712,819 B2 | 3/2004 | Zucherman et al. |
| 6,712,853 B2 | 3/2004 | Kuslich |
| 6,716,245 B2 | 4/2004 | Pasquet et al. |
| 6,716,246 B1 | 4/2004 | Gonzalez |
| 6,716,247 B2 | 4/2004 | Michelson |
| 6,719,794 B2 * | 4/2004 | Gerber et al. ............... 623/17.11 |
| 6,730,088 B2 | 5/2004 | Yeh |
| 6,730,126 B2 | 5/2004 | Boehm et al. |
| 6,733,504 B2 | 5/2004 | Lin et al. |
| 6,733,534 B2 | 5/2004 | Sherman |
| 6,736,821 B2 | 5/2004 | Squires et al. |
| 6,743,255 B2 | 6/2004 | Ferree |
| 6,746,451 B2 | 6/2004 | Middleton et al. |
| 6,746,454 B2 | 6/2004 | Winterbottom et al. |
| 6,746,484 B1 | 6/2004 | Liu et al. |
| 6,755,837 B2 | 6/2004 | Ebner |
| 6,758,863 B2 | 7/2004 | Estes et al. |
| 6,764,491 B2 | 7/2004 | Frey et al. |
| 6,767,366 B2 | 7/2004 | Lee et al. |
| 6,776,798 B2 | 8/2004 | Camino et al. |
| 6,793,679 B2 | 9/2004 | Michelson |
| 6,805,695 B2 | 10/2004 | Keith et al. |
| 6,808,537 B2 | 10/2004 | Michelson |
| 6,814,737 B2 | 11/2004 | Cauthen |
| 6,814,756 B1 | 11/2004 | Michelson |
| 6,821,276 B2 | 11/2004 | Lambrecht |
| 6,827,743 B2 | 12/2004 | Eisermann et al. |
| 6,830,570 B1 | 12/2004 | Frey et al. |
| 6,830,574 B2 | 12/2004 | Heckele et al. |
| 6,833,006 B2 | 12/2004 | Foley et al. |
| 6,837,905 B1 | 1/2005 | Lieberman |
| 6,863,672 B2 | 3/2005 | Reiley et al. |
| 6,875,213 B2 | 4/2005 | Michelson |
| 6,890,355 B2 | 5/2005 | Michelson |
| 6,890,356 B2 | 5/2005 | Ralph et al. |
| 6,893,464 B2 | 5/2005 | Kiester |
| 6,923,811 B1 | 8/2005 | Carl et al. |
| 6,923,813 B2 | 8/2005 | Phillips et al. |
| 6,926,737 B2 | 8/2005 | Jackson |
| 6,929,647 B2 | 8/2005 | Cohen |
| 6,939,318 B2 | 9/2005 | Stenzel |
| 6,945,974 B2 | 9/2005 | Dalton |
| 6,969,404 B2 | 11/2005 | Ferree |
| 6,974,480 B2 | 12/2005 | Messerli et al. |
| 6,976,772 B2 | 12/2005 | Albou et al. |
| 6,986,772 B2 | 1/2006 | Michelson |
| 6,989,031 B2 | 1/2006 | Michelson |
| 7,004,971 B2 | 2/2006 | Serhan et al. |
| 7,018,413 B2 | 3/2006 | Kruger |
| 7,033,394 B2 | 4/2006 | Michelson |
| 7,041,135 B2 | 5/2006 | Michelson |
| 7,056,345 B2 | 6/2006 | Kuslich |
| 7,063,725 B2 | 6/2006 | Foley |
| 7,070,598 B2 | 7/2006 | Lim et al. |
| 7,087,055 B2 | 8/2006 | Lim et al. |
| 7,115,132 B2 | 10/2006 | Errico et al. |
| 7,147,641 B2 | 12/2006 | Chen |
| 7,182,782 B2 | 2/2007 | Kirschman |
| 7,235,081 B2 | 6/2007 | Errico et al. |
| 7,235,082 B2 | 6/2007 | Bartish et al. |
| 7,244,258 B2 | 7/2007 | Burkus et al. |
| 7,354,453 B2 | 4/2008 | McAfee |
| 7,407,513 B2 | 8/2008 | Alleyne |
| 7,500,991 B2 | 3/2009 | Bartish et al. |
| 7,559,930 B2 | 7/2009 | Allard et al. |
| 7,575,580 B2 | 8/2009 | Lim et al. |
| 7,594,931 B2 | 9/2009 | Louis et al. |
| 7,608,080 B2 | 10/2009 | Shipp et al. |
| 7,648,506 B2 | 1/2010 | McCord et al. |
| 7,758,647 B2 | 7/2010 | Arnin et al. |
| 2001/0034553 A1 | 10/2001 | Michelson |
| 2001/0047208 A1 | 11/2001 | Michelson |
| 2002/0013624 A1 | 1/2002 | Michelson |
| 2002/0019637 A1 | 2/2002 | Frey et al. |
| 2002/0022856 A1 | 2/2002 | Johnson et al. |
| 2002/0022886 A1 | 2/2002 | Fuss et al. |
| 2002/0026244 A1 | 2/2002 | Trieu |
| 2002/0055745 A1 | 5/2002 | McKinley et al. |
| 2002/0065558 A1 | 5/2002 | Varga et al. |
| 2002/0065560 A1 | 5/2002 | Varga et al. |
| 2002/0077700 A1 | 6/2002 | Varga et al. |
| 2002/0077701 A1 | 6/2002 | Kuslich |
| 2002/0087212 A1 * | 7/2002 | James et al. ............... 623/17.11 |
| 2002/0091387 A1 | 7/2002 | Hoogland |
| 2002/0091390 A1 | 7/2002 | Michelson |
| 2002/0116006 A1 | 8/2002 | Cohen |
| 2002/0143400 A1 | 10/2002 | Biscup |
| 2002/0151976 A1 | 10/2002 | Foley et al. |
| 2002/0161443 A1 | 10/2002 | Michelson |
| 2002/0165550 A1 | 11/2002 | Frey et al. |
| 2002/0173851 A1 | 11/2002 | McKay |
| 2003/0014118 A1 | 1/2003 | Lambrecht et al. |
| 2003/0023307 A1 | 1/2003 | Michelson |
| 2003/0040796 A1 | 2/2003 | Ferree |
| 2003/0055427 A1 | 3/2003 | Graf |
| 2003/0065394 A1 | 4/2003 | Michelson |
| 2003/0065396 A1 | 4/2003 | Michelson |
| 2003/0074075 A1 | 4/2003 | Thomas et al. |
| 2003/0078668 A1 | 4/2003 | Michelson |
| 2003/0083747 A1 | 5/2003 | Winterbottom et al. |
| 2003/0093155 A1 | 5/2003 | Lambrecht et al. |
| 2003/0105527 A1 | 6/2003 | Bresina et al. |
| 2003/0125739 A1 | 7/2003 | Bagga et al. |
| 2003/0135275 A1 | 7/2003 | Garcia et al. |
| 2003/0135279 A1 | 7/2003 | Michelson |
| 2003/0139816 A1 | 7/2003 | Michelson |
| 2003/0149438 A1 | 8/2003 | Nichols et al. |
| 2003/0149482 A1 | 8/2003 | Michelson |
| 2003/0176926 A1 | 9/2003 | Boehm et al. |
| 2003/0195630 A1 | 10/2003 | Ferree |
| 2003/0199979 A1 | 10/2003 | McGuckin |
| 2003/0199983 A1 | 10/2003 | Michelson |
| 2003/0208203 A1 | 11/2003 | Lim et al. |
| 2003/0229358 A1 | 12/2003 | Errico et al. |
| 2004/0002719 A1 | 1/2004 | Oz et al. |
| 2004/0030346 A1 | 2/2004 | Frey et al. |
| 2004/0030392 A1 | 2/2004 | Lambrecht et al. |
| 2004/0039392 A1 | 2/2004 | Trieu |
| 2004/0044412 A1 | 3/2004 | Lambrecht |
| 2004/0073217 A1 | 4/2004 | Michelson |
| 2004/0082999 A1 * | 4/2004 | Mathys et al. ............. 623/17.11 |
| 2004/0097980 A1 | 5/2004 | Ferree |
| 2004/0117019 A1 | 6/2004 | Trieu et al. |
| 2004/0117020 A1 | 6/2004 | Frey et al. |
| 2004/0127990 A1 | 7/2004 | Bartish et al. |
| 2004/0127992 A1 | 7/2004 | Serhan et al. |
| 2004/0133280 A1 | 7/2004 | Trieu |
| 2004/0153065 A1 | 8/2004 | Lim |
| 2004/0167538 A1 | 8/2004 | Gerber et al. |
| 2004/0193270 A1 | 9/2004 | DiMauro et al. |
| 2004/0193271 A1 | 9/2004 | Fraser et al. |
| 2004/0199254 A1 | 10/2004 | Louis et al. |
| 2004/0210313 A1 | 10/2004 | Michelson |
| 2004/0210315 A1 | 10/2004 | Li et al. |
| 2004/0225286 A1 | 11/2004 | Elliott |

| | | |
|---|---|---|
| 2004/0225289 A1 | 11/2004 | Biedermann et al. |
| 2004/0225361 A1 | 11/2004 | Glenn et al. |
| 2004/0249461 A1 | 12/2004 | Ferree |
| 2004/0249466 A1 | 12/2004 | Liu et al. |
| 2004/0260397 A1 | 12/2004 | Lambrecht |
| 2004/0267269 A1 | 12/2004 | Middleton et al. |
| 2004/0267368 A1 | 12/2004 | Kuslich |
| 2005/0015140 A1 | 1/2005 | deBeer |
| 2005/0027360 A1 | 2/2005 | Webb et al. |
| 2005/0033305 A1 | 2/2005 | Schultz |
| 2005/0038431 A1 | 2/2005 | Bartish et al. |
| 2005/0038513 A1 | 2/2005 | Michelson |
| 2005/0049708 A1 | 3/2005 | Atkinson et al. |
| 2005/0065609 A1 | 3/2005 | Wardlaw |
| 2005/0070900 A1 | 3/2005 | Serhan et al. |
| 2005/0080422 A1 | 4/2005 | Otte et al. |
| 2005/0090824 A1 | 4/2005 | Shluzas et al. |
| 2005/0096745 A1 | 5/2005 | Andre et al. |
| 2005/0113838 A1 | 5/2005 | Phillips et al. |
| 2005/0113920 A1 | 5/2005 | Foley et al. |
| 2005/0119747 A1 | 6/2005 | Fabris et al. |
| 2005/0131419 A1 | 6/2005 | McCord et al. |
| 2005/0131420 A1 | 6/2005 | Techiera et al. |
| 2005/0131536 A1 | 6/2005 | Eisermann et al. |
| 2005/0137448 A1 | 6/2005 | Wingler et al. |
| 2005/0143749 A1 | 6/2005 | Zalenski et al. |
| 2005/0143822 A1* | 6/2005 | Paul .......................... 623/17.16 |
| 2005/0143827 A1 | 6/2005 | Globerman et al. |
| 2005/0149194 A1 | 7/2005 | Ahlgren |
| 2005/0149195 A1 | 7/2005 | Boyd et al. |
| 2005/0149197 A1 | 7/2005 | Cauthen |
| 2005/0154459 A1 | 7/2005 | Wolek et al. |
| 2005/0154460 A1 | 7/2005 | Yundt |
| 2005/0159817 A1 | 7/2005 | Ferree |
| 2005/0171552 A1 | 8/2005 | Johnson et al. |
| 2005/0171554 A1 | 8/2005 | Estes et al. |
| 2005/0171609 A1 | 8/2005 | Humphreys et al. |
| 2005/0187625 A1 | 8/2005 | Wolek et al. |
| 2005/0187629 A1 | 8/2005 | Michelson |
| 2005/0222684 A1 | 10/2005 | Ferree |
| 2005/0228500 A1 | 10/2005 | Kim et al. |
| 2005/0261681 A9 | 11/2005 | Branch et al. |
| 2005/0278027 A1 | 12/2005 | Hyde et al. |
| 2006/0004376 A1 | 1/2006 | Shipp et al. |
| 2006/0004456 A1 | 1/2006 | McKay |
| 2006/0058793 A1 | 3/2006 | Michelson |
| 2006/0064102 A1 | 3/2006 | Ebner |
| 2006/0074427 A1 | 4/2006 | Lieberman |
| 2006/0100705 A1* | 5/2006 | Puno et al. ................. 623/17.11 |
| 2006/0129244 A1 | 6/2006 | Ensign |
| 2006/0142858 A1 | 6/2006 | Colleran et al. |
| 2006/0178673 A1 | 8/2006 | Curran |
| 2006/0190083 A1 | 8/2006 | Arnin et al. |
| 2006/0200139 A1 | 9/2006 | Michelson |
| 2006/0200164 A1 | 9/2006 | Michelson |
| 2006/0229627 A1 | 10/2006 | Hunt et al. |
| 2006/0235426 A1 | 10/2006 | Lim et al. |
| 2006/0241641 A1 | 10/2006 | Albans et al. |
| 2006/0241760 A1* | 10/2006 | Randall et al. ............. 623/17.11 |
| 2006/0241761 A1 | 10/2006 | Gately |
| 2007/0010826 A1 | 1/2007 | Rhoda et al. |
| 2007/0038216 A1 | 2/2007 | Hamada |
| 2007/0067035 A1 | 3/2007 | Falahee |
| 2007/0093904 A1 | 4/2007 | Biedermann et al. |
| 2007/0123985 A1 | 5/2007 | Errico et al. |
| 2007/0142843 A1 | 6/2007 | Dye |
| 2007/0162128 A1* | 7/2007 | DeRidder et al. .......... 623/17.11 |
| 2007/0225726 A1 | 9/2007 | Dye et al. |
| 2007/0225808 A1 | 9/2007 | Warnick |
| 2007/0260314 A1 | 11/2007 | Biyani |
| 2007/0276406 A1 | 11/2007 | Mahoney et al. |
| 2008/0009880 A1 | 1/2008 | Warnick et al. |
| 2008/0065220 A1 | 3/2008 | Alleyne |
| 2008/0065221 A1 | 3/2008 | Alleyne |
| 2008/0077153 A1 | 3/2008 | Pernsteiner et al. |
| 2008/0125865 A1 | 5/2008 | Abdelgany |
| 2008/0140205 A1 | 6/2008 | Richelsoph |
| 2008/0140206 A1 | 6/2008 | Felt |
| 2009/0270990 A1 | 10/2009 | Louis et al. |
| 2009/0276049 A1* | 11/2009 | Weiland .................... 623/17.16 |

FOREIGN PATENT DOCUMENTS

| | | |
|---|---|---|
| EP | 1124510 | 12/2004 |
| WO | WO-9526164 | 10/1995 |
| WO | WO-9720526 | 6/1997 |
| WO | 9801091 A1 | 1/1998 |
| WO | WO-9909913 | 3/1999 |
| WO | WO-9963914 | 12/1999 |
| WO | WO-0024343 | 5/2000 |
| WO | WO-0025687 | 5/2000 |
| WO | WO-0066045 | 11/2000 |
| WO | WO-0128465 | 4/2001 |
| WO | WO-0128468 | 4/2001 |
| WO | WO-0217823 | 3/2002 |
| WO | WO-0226144 | 4/2002 |
| WO | WO-02058594 | 8/2002 |
| WO | WO-02058599 | 8/2002 |
| WO | WO-2004098466 | 11/2004 |
| WO | WO-2005009299 | 2/2005 |

* cited by examiner

OFFSET RADIUS LORDOSIS

CROSS-REFERENCE TO RELATED APPLICATIONS

This application relates to, and claims the benefit of the filing date of, co-pending U.S. provisional patent application Ser. No. 60/825,089 entitled "OFFSET RADIUS LORDOSIS," filed Sep. 8, 2006, the entire contents of which are incorporated herein by reference for all purposes. This application also relates to co-pending U.S. provisional patent application No. 60/825,084 entitled INSTRUMENTS FOR DELIVERING SPINAL IMPLANTS, filed Sep. 8, 2006, and to U.S. patent application Ser. No. 11/690,692 entitled INSTRUMENTS FOR DELIVERING SPINAL IMPLANTS, filed Mar. 23, 2007, the entire contents of which are incorporated herein by reference for all purposes.

TECHNICAL FIELD

The invention relates generally to surgical instruments and devices and, more particularly, to spacers to be inserted into an intervertebral space of the human spine.

BACKGROUND

The human spine is a complex structure designed to achieve a myriad of tasks, many of them of a complex kinematic nature. The spinal vertebrae allow the spine to flex in three axes of movement relative to the portion of the spine in motion. These axes include the horizontal (i.e., bending either forward/anterior or aft/posterior), roll (i.e., lateral bending to either the left or right side) and rotation (i.e., twisting of the shoulders relative to the pelvis).

The intervertebral spacing (i.e., between neighboring vertebra) in a healthy spine is maintained by a compressible and somewhat elastic disc. The disc serves to allow the spine to move about the various axes of rotation and through the various arcs and movements required for normal mobility. The elasticity of the disc maintains spacing between the vertebrae, allowing room or clearance for compression of neighboring vertebrae, during flexion and lateral bending of the spine. In addition, the disc allows relative rotation about the vertical axis of neighboring vertebrae, allowing twisting of the shoulders relative to the hips and pelvis. Clearance between neighboring vertebrae, typically maintained by a healthy disc, is also important to allow nerves from the spinal cord to extend out of the spine between neighboring vertebrae without being squeezed or impinged by the vertebrae.

In situations (e.g., based upon injury or otherwise) where a disc is not functioning properly, the inter-vertebral disc tends to compress, and in doing so pressure is exerted on nerves extending from the spinal cord by this reduced inter-vertebral spacing. Various other types of nerve problems may be experienced in the spine, such as exiting nerve root compression in neural foramen, passing nerve root compression, and enervated annulus (where nerves grow into a cracked/compromised annulus, causing pain every time the disc/annulus is compressed), as examples.

Many medical procedures have been devised to alleviate such nerve compression and the pain that results from nerve pressure. Many of these procedures revolve around methods to prevent the vertebrae from moving too close to each other by surgically removing an improperly functioning disc and replacing the improperly functioning disc with a lumbar interbody fusion device or spacer. Although prior interbody devices, including spacers, can be effective at improving patient condition, a significant amount of time is required for recovery from the surgery and for ultimately fusing the adjacent vertebrae together with the aid of the device. Damage or deterioration of the disc(s) may also cause distortion of the normal curvature of the spine. Indeed, it is known that the lordosis and kyphosis of the spine can be affected by irregular discs.

Generally speaking, reducing the time that is required for the patient to recover from the operation and for the vertebra to fuse together will reduce patient discomfort and hasten the day that the patient can resume normal activities. What is needed, therefore, are spacers that promote recovery and bone fusion.

SUMMARY

In an embodiment of the present invention, a vertebral body replacement or spacer is provided that can re-create a lordosis angle (or other angle) of a human spine. The spacer of the current embodiment includes contoured superior and inferior surfaces. More particularly, the contoured surfaces can be defined by a first radii and a second radii substantially orthogonal to the first radii. Thus, the bearing surfaces can better conform to the concave end plates of the adjacent vertebra.

In another embodiment the present invention provides a method of re-creating a lordosis angle. The method includes inserting a spacer into an intervertebral space and positioning the spacer in such a manner that the contoured bearing surfaces of the spacer generally correspond to the ends of the adjacent vertebra. Of course, the spacers and methods of the current embodiment can be used to create other angles in the human spine.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1A:
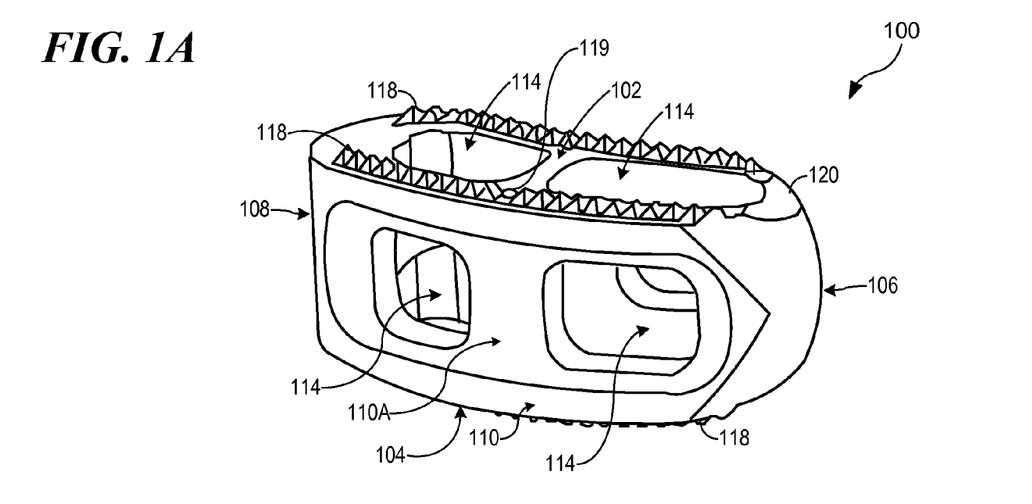
FIG. 1A illustrates an upper oblique view of a spacer constructed in accordance with an embodiment of the present invention as seen from a medial end and a anterior side of the spacer.
Figure 1B:
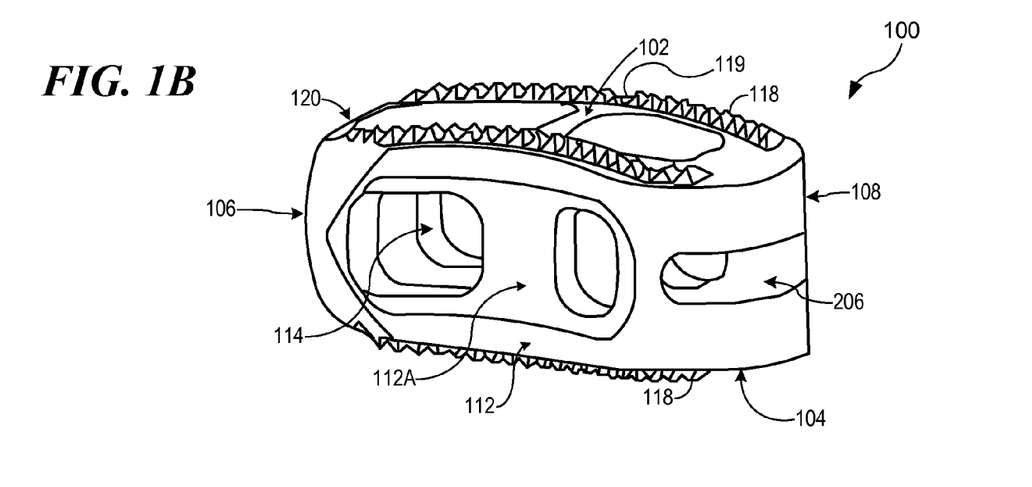
FIG. 1B illustrates an upper oblique view of the spacer of FIG. 1A as seen from the lateral end and posterior side of the spacer.

Referring to FIGS. 1A and 1B, of the drawings, the reference numeral 100 generally designates an embodiment of a spacer 100 according to the present invention. The spacer 100 may be formed as a single continuous piece. Additionally, the spacer 100 may be used to help restore the lordosis angle of a spine (e.g., a human spine). Accordingly, the spacer 100 may be designed to be secured to an insertion instrument, inserted into an intervertebral space, positioned therein, and either released or withdrawn, based upon the actions of a surgeon or other qualified user. As a result, the spacer 100 may comprise features that enable the insertion instrument to hold, rotate, and release the spacer 100. Furthermore, the spacer 100 may be configured in such a manner that the spacer 100 may substantially and efficiently fill an intervertebral space, including the cavities defined by the concave end plates (or the ends) of the adjacent vertebra.

More particularly, as seen in FIG. 1A, the spacer 100 may comprise a superior bearing surface 102, an inferior bearing face 104, a nose or medial end 106, an lateral end 108, a anterior side 110, and a posterior side 112 (more clearly shown in FIG. 1B). The spacer 100 may define an interior cavity 114 that penetrates or extends through the sides 110 and 112 and bearing surfaces 102 and 104. The interior cavity 114 may comprise one or more openings and chambers depending upon the configuration (e.g., the spacer 100 shown in FIGS. 1A and 1B comprises two chambers and eight openings). Additionally, the sides 110 and 112 of the spacer 100 may respectively comprise recessed or concave areas such as a anterior recess 110A (FIG. 1A) and a posterior recess 112A (FIG. 1B). The anterior side 110 and the posterior side 112 may be defined by a first and second radius (not shown) extending from a coincident radial origin.

The spacer 100 may comprise a plurality of similarly configured engaging protrusions 118 (e.g., rows of teeth) following the contours of the bearing surfaces 102 and 104. The engaging protrusions 118 may engage the abutting surfaces of the adjacent vertebra, thereby helping to retain the spacer 100 within the inter-vertebral space. The illustrative embodiment of the spacer 100 comprises two rows of engaging protrusions 118 following the contours of each of the bearing surfaces 102 and 104. Each of the individual teeth may comprise a small flat surface at the tip of each tooth, substantially parallel to the corresponding bearing surface 102 and 104. The flat surface may offer an advantage in distributing the load across a wider area of the adjacent vertebral surface after insertion of the spacer 100. In addition, the flat surface may also increase the relative strength of the teeth and reduce the potential for contamination that could be otherwise be caused by the adjacent vertebral surfaces shearing or breaking off pointed individual tips of the teeth. In some embodiments, the teeth are positioned symmetrically about a midline of the spacer 100. However, an embodiment of the spacer 100 may not be limited to this configuration. Various locations and configurations of engaging protrusions 118 on either or both of the bearing surfaces 102 and 104 may be used.

In some embodiments, the spacer 100 may be made from a radiolucent material selected from the polyaryl ether ketone family (PAEK), such as polyether ether ketone (PEEK) or polyether ketone ketone (PEKK). In such a case, the spacer 100 may also comprise one or more radiopaque markers 119 (e.g., pins, screws, spheres, among others), such as tantalum for example, from among other types of appropriate material. The markers 119 may enable a technician to locate the spacer 100. The markers 119 may enable a technician to determine the location of an in vivo spacer 100 on a fluoroscope, since the marker 119 will appear in the image on the screen. Otherwise, a spacer 100 made of a radiolucent material may be difficult to locate after being inserted in vivo. However, a spacer 100 may also be made of radiopague material such as titanium, among others. In the case of a radiopaque material, a marker 119 may not be needed to locate the position of the spacer 100 via a fluoroscope. With respect to material selection, an advantage to using a material selected from the PAEK family for a spacer 100 is that the modulus of the material is similar to the modulus of the surrounding bone. If a material such as titanium is used, the spacer 100 may shield the bone from a majority of stress, which may adversely effect the healing of bone.

Figure 4:
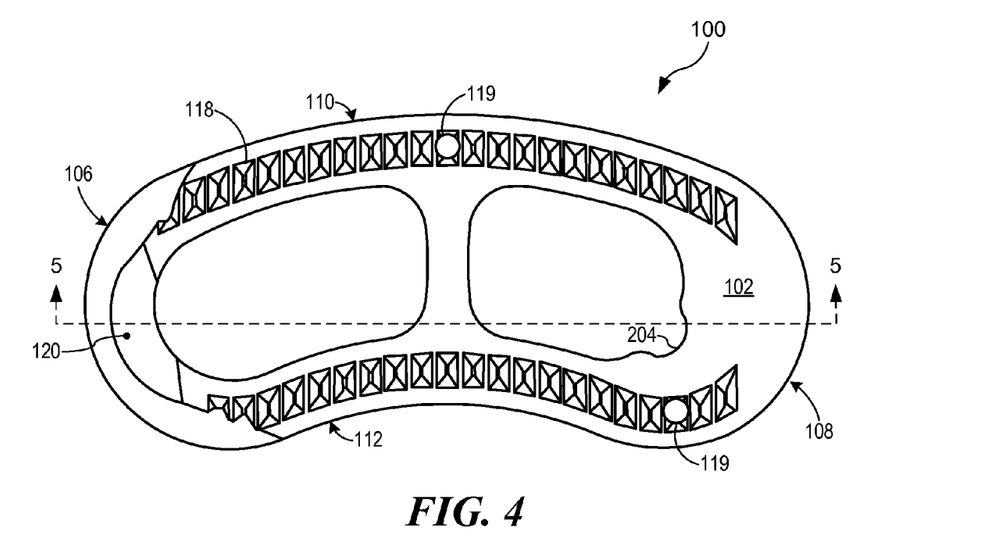
FIG. 4 illustrates a top view of the spacer of FIG. 1B.

The markers 119 may be added after the main body of the spacer 100 is formed. An example of a method used to couple the markers 119 to the spacer 100 may be to drill holes in the spacer 100 and then secure the markers 119 within the holes. However, an embodiment of the spacer 100 may not be limited to this method. Other methods, such as forming or molding the spacer 100 around a marker 119, chemically adhering the marker 119 to a surface or cavity of the spacer 100, or mechanically attaching a marker 119 to the spacer 100, among others, may provide a locating device for later detection of an inserted spacer 100. As seen in FIG. 4, some locations for the marker 119 may be along the midpoint of the spacer 100 and/or at the attachment slot 206/insertion port 204 located in the lateral end 108. Locating a marker 119 at or proximate to the attachment slot 206 may allow a technician to locate the attachment slot 206 of a previously inserted spacer 100, thereby enabling the technician to re-attach an instrument 200 (see FIGS. 7A and 7B) to the inserted spacer 100 for removal or repositioning. In certain embodiments, the marker 119 may be substantially perpendicular (for example 90 degrees plus or minus 45 degrees or more specifically 90 degrees plus or minus 15 degrees) to the attachment slot 206 which may allow a technician to easily locate, orientate and reattach an insertion instrument 200 (see FIGS. 7A and 7B) to the attachment slot 206 to reposition the spacer 100. In some illustrative embodiments, the markers 119 may be oriented substantially perpendicular to the superior and/or inferior surfaces 102, 104.

The interior cavities 114 may be filled with bone chips or a bone growth material prior to inserting the spacer 100 into the intervertebral space of a spine. The bone chips or the bone growth material may encourage bone growth to envelop and fill the spacer 100. As a result, the new bone material may thereby fuse the vertebra together. Therefore, the volumes of the cavity 114, the anterior recess 110A, and the posterior recess 112A, may typically be maximized, provided that the remaining body of the spacer 100 maintains sufficient strength to absorb the loads that will most likely be placed on the spine. In certain embodiments, the width of a cavity 114 in a transverse direction may be greater than either of the transverse widths of each of walls forming the posterior and anterior sides of the cavity 114. The interior cavities 114 may generally follow an offset from the exterior walls of the spacer 100. The middle section of some embodiments of the spacer 100 may substantially form an I-beam configuration in order to add strength to the spacer 100.

The spacer 100 may be inserted into a relatively narrow gap between adjacent vertebrae. Therefore, the medial end 106 of the spacer 100 may be configured to have a "bullet" or streamline shape (as more easily seen in FIG. 1A). The convex, slightly pointed shape (i.e., substantially semi-spheroidal) of the medial end 106 may enable the surgeon to seat the spacer 100 both on and between the vertebra, prior to possibly striking the insertion instrument to drive the spacer 100 further into the intervertebral space. The rounded wedge-like shape of the medial end 106 may assist in inserting the spacer 100 between the vertebrae. For much the same reason that the medial end 106 may be bullet shaped, an angled landing 120 may be provided at a juncture of the superior (and/or inferior) surfaces 102 and 104, and the medial end 106. The angled landing 120 may be symmetrically applied to the medial end 106 of the spacer 100 relative to a centerline.

Turning now to FIG. 1B, the spacer 100 may comprise an attachment slot 206 for securing the spacer 100 to an insertion instrument. More particularly, the spacer 100 may be secured to an embodiment of an insertion instrument disclosed in a co-pending U.S. patent application Ser. No. 11/690,692 entitled INSTRUMENTS FOR DELIVERING SPINAL IMPLANTS, filed Mar. 23, 2007, and incorporated herein as if set forth in full. Once attached to a spacer 100, an insertion instrument may then be used to insert the spacer 100 into an intervertebral space (or other space in vivo), position the spacer 100, and either release or withdraw the spacer 100 from the space.

Figure 1C:
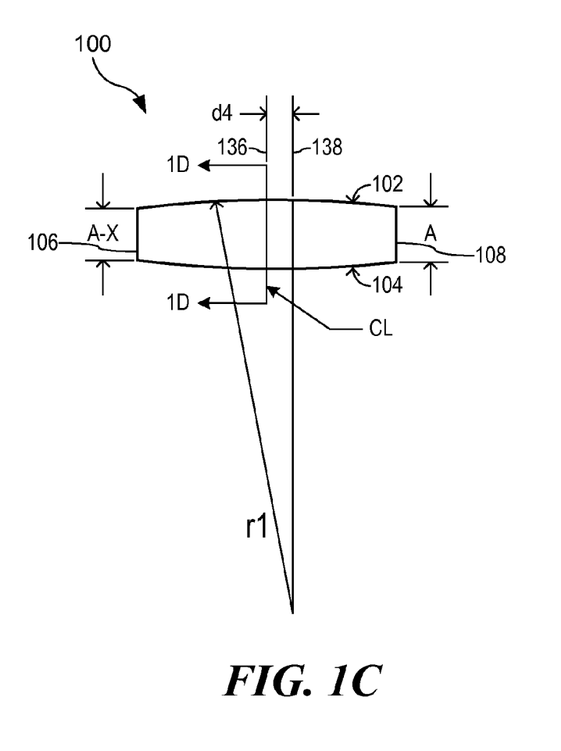
FIG. 1C illustrates a simplified longitudinal view of the spacer of FIG. 1A.
Figure 1D:
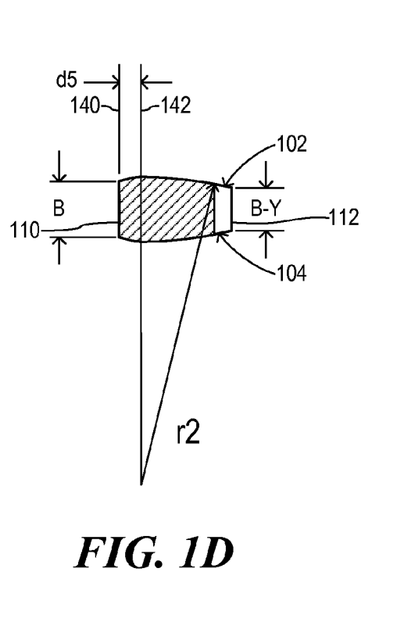
FIG. 1D illustrates a simplified cross-sectional view of the spacer of FIG. 1C, as seen along line 1D-1D.

Referring now to FIGS. 1C and 1D, an illustrative embodiment of the spacer 100 may be configured to more thoroughly and effectively fill the space between the concave ends of adjacent vertebra. Either or both of the bearing surfaces 102 and 104 may be defined by compound curves. In the interest of conserving space, only the superior bearing surface 102 may be described in detail. However, the information may be applied to inferior bearing surface 104 in addition to or in place of superior bearing surface 102. The two sets of radii may be described as longitudinal and transverse for the ease of description. The longitudinal radius "r1" may be substantially orthogonal to the transverse radius "r2." However, substantially orthogonal may include an angular range from perpendicular to slightly less than parallel. One illustrative angular range may be 90° plus or minus 45°. Another exemplary angular range may be a range of 90° plus or minus 15°. More than one radius may be used for each of the longitudinal radius and the transverse radius.

As seen in FIG. 1C, the superior bearing surface 102 may curve in a circular manner as defined by a longitudinal radius "r1" and a longitudinal offset distance "d4." The longitudinal offset "d4" may be to either side of a longitudinal center 136 of the spacer 100 in an medial-lateral direction. Therefore, the longitudinal radius "r1" may generally be perpendicular to the superior bearing surface 102 at a distance approximately "d4" to one side of the longitudinal center 136 of the spacer 100 (e.g., at the longitudinal radial location 138). Alternatively, the longitudinal radius "r1" may also be coincident to the longitudinal center 136 of the spacer 100 for a longitudinal offset "d4" of zero.

In the illustrative case shown in FIG. 1C, the longitudinal offset distance "d4" is offset from the longitudinal center 136 in the lateral direction (e.g., toward the lateral end 108). Consequently, the width of the lateral end 108 may be approximated by dimension A, and the width of the medial end 106 may be approximated by a dimension A-X. For the example shown, the medial end 106 may be smaller than the medial end 108.

As seen in FIG. 1D, an illustrative embodiment of the superior bearing surface 102 may be defined by a transverse radius "r2," nominal transverse center 140, transverse offset "d5," and transverse radial location 142. The transverse nominal center 140 may be coincident with the anterior side 110. The transverse offset "d5" may be to either side of the transverse nominal center 140 (e.g., at the transverse radial location 142). Preferably, the transverse radius "r2" may also be coincident to the transverse nominal center 140 of the spacer 100 for a transverse offset "d5" of zero.

In the illustrative case shown in FIG. 1D, the transverse offset "d5" is offset from the nominal transverse center 140 in the posterior direction (e.g., toward the posterior side 112). Consequently, the width of the anterior side 110 may be approximated by dimension B, and the width of the posterior side 112 may be approximated by a dimension B-Y. For the example shown, the posterior side 112 may be smaller than the anterior side 110.

The superior bearing surface 102 may have a local maximum height at an intersection of the medial-lateral longitudinal radial location 138 and the anterior-posterior transverse radial location 142. However, the offsets "d4" and "d5" may be zero, in which case the local maximum height occurs at a center of the spacer 100 in the medial-lateral direction on the anterior side 110. Similarly, the inferior bearing surface 104 may also be defined by a compound curve with offset radii. Of course, more complex curves such as curves defined by multiple radii (or simpler curves) may define the surfaces 102 and 104 without departing from the scope of the present invention.

Figure 1E:
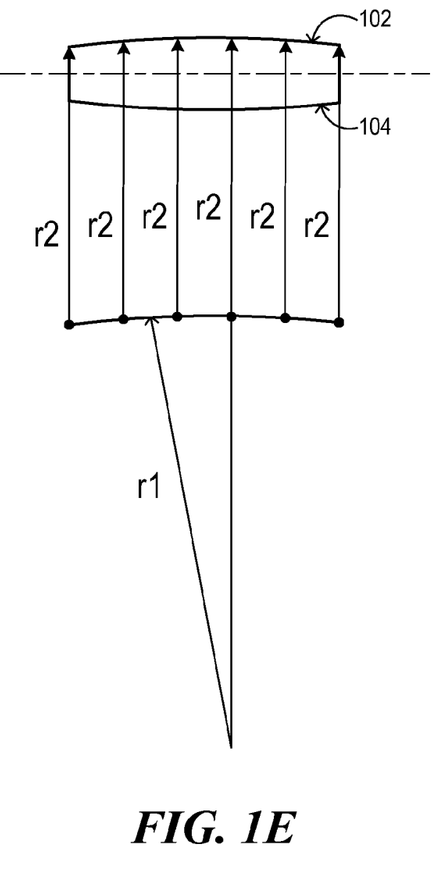
FIG. 1E illustrates a descriptive view of the spacer of FIG. 1C.

Turning now to FIG. 1E, the transverse radii "r2" may remain relatively constant along the longitudinal direction when viewed along a transverse direction. As a result, each of the transverse radii "r2" may have a radial origin at a different location relative to a nominally horizontal plane (as seen in this view) bi-secting the distance between the superior bearing surface 102 and the inferior bearing surface 104. The corresponding radial origins of the transverse radii "r2" may follow a curve (e.g., as defined by the longitudinal radius "r1" for the particular longitudinal cross-section) of the superior bearing surface 102 along the longitudinal direction. Of course, the radial origins corresponding to the transverse radii "r2" may also be contained within a single plane. In such a case, the surface of the superior bearing surface 102 may only be defined by the transverse radii "r2." The cross-sectional representation of the superior bearing surface 102 along the longitudinal direction would be straight.

Figure 1F:
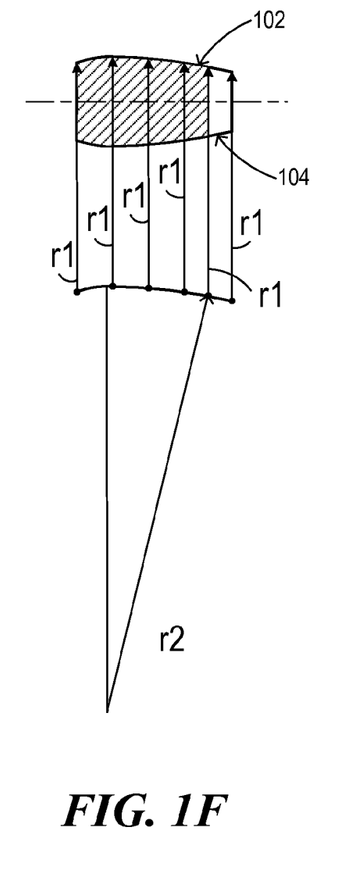
FIG. 1F illustrates a descriptive view of the spacer of FIG. 1D.

Turning now to FIG. 1F, the longitudinal radii "r1" may remain relatively constant along the transverse direction when viewed along a longitudinal direction. As a result, each of the longitudinal radii "r1" may have a radial origin at a different location relative to a nominally horizontal plane (as seen in this view) bisecting the distance between the superior bearing surface 102 and the inferior bearing surface 104. The corresponding radial origins of the longitudinal radii "r1" may follow a curve (e.g., as defined by the longitudinal radius "r1" for the particular longitudinal cross-section) of the superior bearing surface 102 along the longitudinal direction. Of course, the radial origins corresponding to the longitudinal radii "r2" may also be contained within a single plane. In such a case, the surface of the superior bearing surface 102 may only be defined by the longitudinal radii "r1." The cross-sectional representation of the superior bearing surface 102 along the longitudinal direction would be straight.

Figure 2:
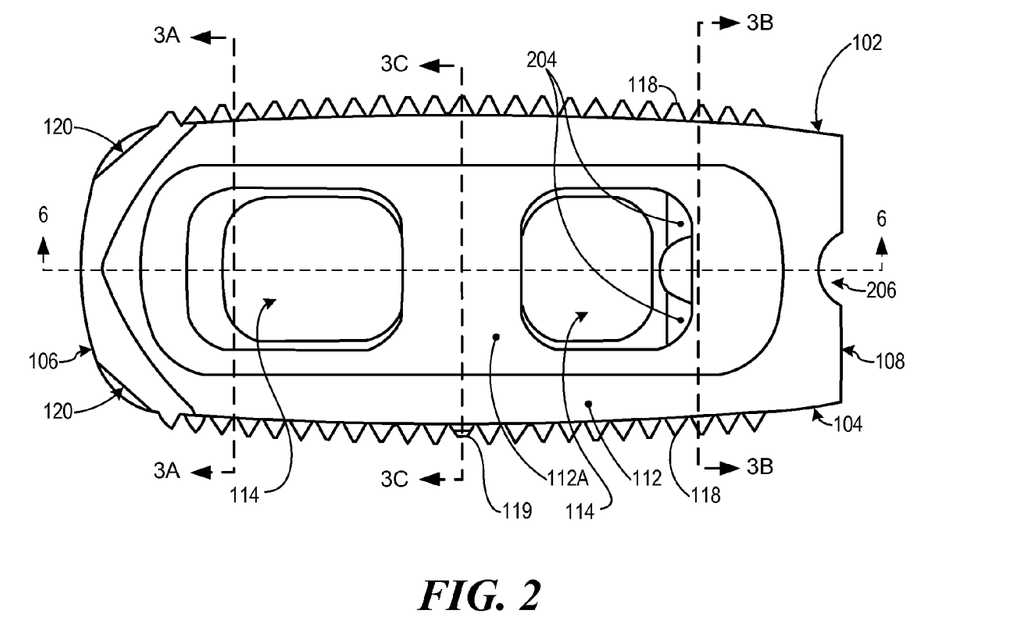
FIG. 2 illustrates a posterior side view of the spacer of FIG. 1B.

Turning now to FIG. 2, an illustrative embodiment of the spacer 100 is shown from a posterior side. The spacer 100 may comprise the superior bearing surface 102, the inferior bearing surface 104, the medial end 106, the lateral end 108, the posterior side 112, the posterior recess 112A, interior cavities 114, and angled landings 120.

The angled landings 120 may be more clearly seen in this view as respectively extending from the superior bearing surface 102 and the inferior bearing surface 104, to join the medial end 106. Two angled landings 120 may be used in this embodiment. However, some embodiments may comprise one angled landing 120 at either the superior bearing surface 102 or the inferior bearing surface 104. Alternatively, the angled landings 120 may provide a transition from the sides 110, 112 to the medial end 106, either in addition to or in place of the angled landings 120 shown in FIG. 2.

The spacer 100 may comprise a plurality of engagement protrusions 118 provided along the superior bearing surface 102 and the inferior bearing surface 104 in addition to one or more markers 119 (only one marker 119 is visible in this view). The plurality of engagement protrusions 118 may extend substantially along the length of the spacer 100 in an medial-lateral direction. At least in part because of the compound curvature of the superior bearing surface 102 and the inferior bearing surface 104 (on which the plurality of engagement protrusions 118 may be located), the engagement protrusions 118 may more readily engage the concave ends of the vertebra. A marker 119 may be provided midway along the length in the medial-lateral direction on the inferior bearing surface 104. However, other locations and multiple markers 119 may be used to more accurately and easily identify the position and orientation of the spacer 100 in vivo.

The spacer 100 may comprise an attachment slot 206 located on an lateral end 108. In addition, the spacer 100 may comprise an insertion port 204 located within an interior cavity 114 of the spacer 100. A portion of the attachment slot 206 and the insertion port 204 may be seen through the interior cavity 114 proximate to the lateral end 108 of the spacer 100. The attachment slot 206 and the insertion port 204 will be described in more detail later.

Figure 3A:
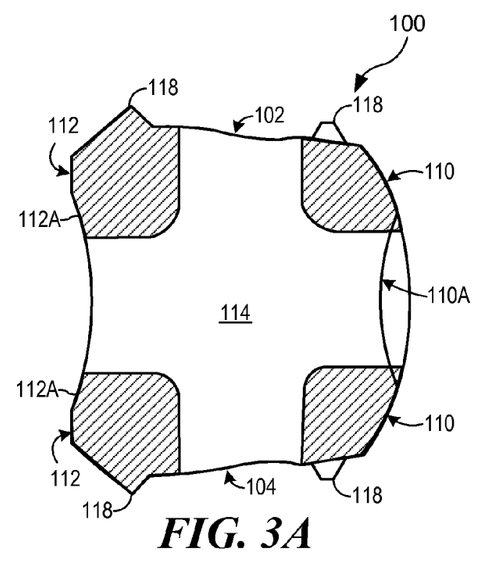
FIG. 3A illustrates a cross-sectional view of the spacer of FIG. 2 as seen along line 3A-3A.

Referring now to FIG. 3A, this figure illustrates a cross-sectional view of the spacer 100 shown in FIG. 2 and taken along line 3A-3A. The cross-section is taken near the medial end 106 (FIG. 2) of the spacer 100. As shown, the posterior recess 112A may be concave and extend further inward than the posterior side 112. Similarly, the anterior recess 110A may also be concave and extend further inward than the anterior side 110. An interior cavity 114 may extend through the superior bearing surface 102, the inferior bearing surface 104, the anterior side 110, and the posterior side 112. In addition, the engagement protrusions 118 may be located the superior bearing surface 102 and the inferior bearing surface 104.

Figure 3B:
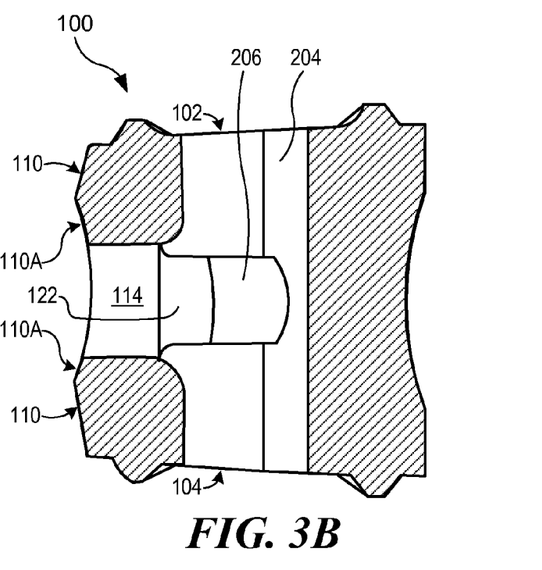
FIG. 3B illustrates a cross-sectional view of the spacer of FIG. 2 as seen along the line 3B-3B.

Turning now to FIG. 3B, this figure illustrates a cross-sectional view of the spacer 100 shown in FIG. 2 and taken along line 3B-3B. The cross-section is taken near the lateral end 108(FIG. 2) of the spacer 100. The interior cavity 114 is shown as extending through the superior bearing surface 102, the inferior bearing surface 104, and the anterior side 110. The anterior recess 110A may be proximate to the interior cavity 114 on the anterior side 110. Additionally, the spacer 100 may comprise a slot wall 122, an insertion port 204, and an attachment slot 206. These elements will be explained later.

Figure 3C:
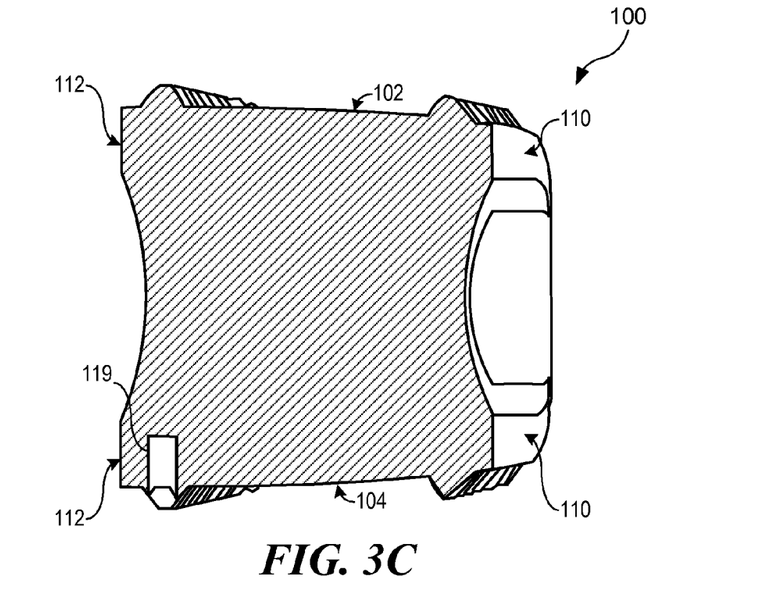
FIG. 3C illustrates a cross-sectional view of the spacer of FIG. 2 as seen along line 3C-3C.

Referring now to FIG. 3C, this figure illustrates a cross-sectional view of the spacer 100 shown in FIG. 2 and taken along line 3C-3C. The cross-section is taken near the mid-point of the spacer 100 relative to the medial-lateral direction. The inferior bearing surface 104 of the spacer 100 may comprise a cylindrical cavity containing a marker 119. As previously detailed, the marker 119 may more readily enable the detection and identification of the spacer 100 in vivo. As more easily seen in this view, the superior bearing surface 102 and the inferior bearing surface 104 may not be substantially parallel to each other. The two surfaces 102, 104 may be angled towards one another in the medial-anterior direction such that the anterior side 110 may be smaller than the posterior side 112.

Turning now to FIG. 4, this figure illustrates a top view of an illustrative embodiment of a spacer 100. The spacer 100 comprises a superior bearing surface 102, medial end 106, lateral end 108, angled landing 120 (only one angled landing 120 is visible in this view). In addition, the spacer 100 may comprise a plurality of engagement protrusions 118 arranged substantially in two rows for example. Each row of engagement protrusions 118 respectively follows the contours of the anterior side 110 and the posterior side 112. Two markers 119 are shown in this exemplary embodiment. One marker 119 may be located within a row of engagement protrusions 118 proximate to the anterior side 110 and mid-way in a medial-lateral direction, for example. Another marker 119 may be located within a row of engagement protrusions 118 proximate to the posterior side 112 and the lateral end 108. This marker 119 may be used by a technician using a fluoroscope to identify the attachment slot 206 (FIG. 5) and/or insertion port 204 of an inserted spacer 100. Using the marker 119 near the lateral end 108 as a guide, the spacer 100 may be reattached to an instrument 200 (FIGS. 7A & 7B) for repositioning and/or removal. Two markers 119 are shown in this illustrative embodiment, however, the quantity and location of markers 119 may be configured as required for enabling location and identification of the spacer 100 in vivo.

Figure 5:
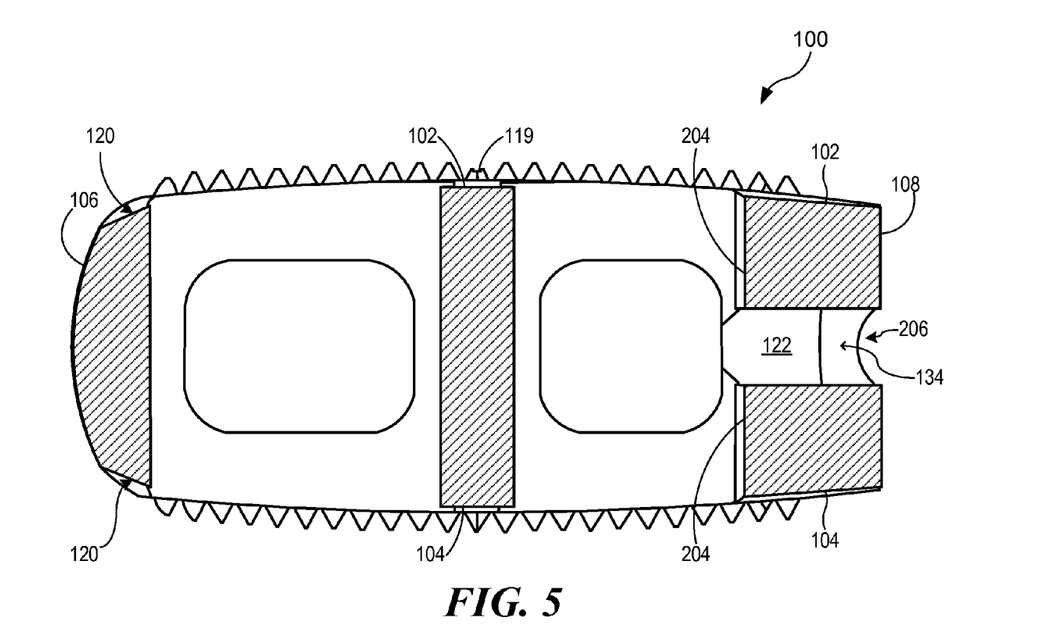
FIG. 5 illustrates a cross-sectional view of the spacer of FIG. 4 as seen along line 5-5.

Referring now to FIG. 5, this figure illustrates a cross-section of FIG. 4 as viewed along line 5-5. The spacer 100 may comprise upper and lower angled landings 120 provided at the medial end 106. The upper angled landing 120 may provide an angled transition from the medial end 106 to the superior bearing surface 102. The lower angled landing 120 may provide an angled transition from the lateral end 108 to the inferior bearing surface 104. In addition, the spacer 100 may comprise a marker 119 provided on the superior bearing surface 102 at approximately the middle of the spacer 100 relative to the medial-lateral direction. The spacer 100 may further comprise a slot wall 122, abutment wall 134, insertion port 204, and attachment slot 206, all located proximate to the lateral end 108.

Figure 6A:
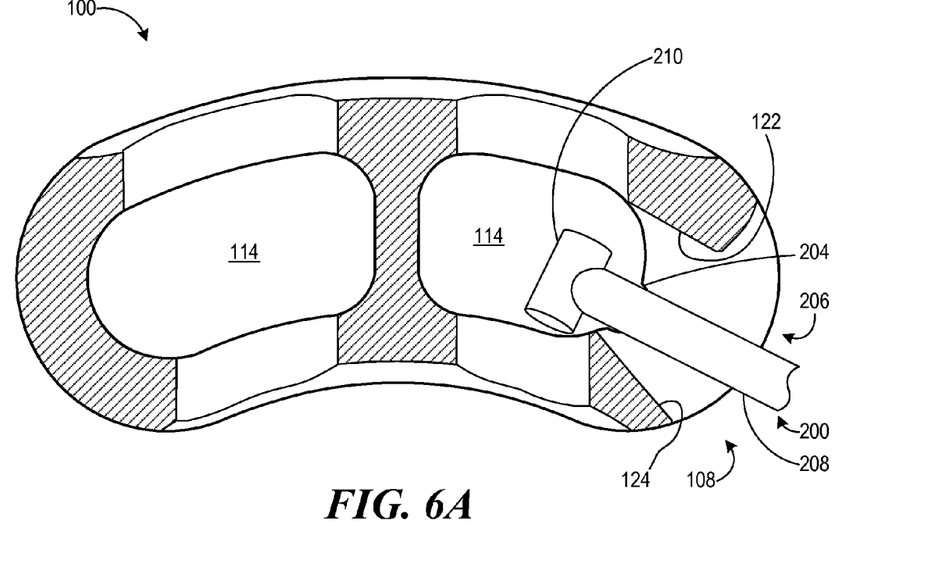
FIG. 6A illustrates a detailed cross-sectional view of the spacer of FIG. 2, as seen along line 6-6, and illustrating an insertion instrument in a released position.
Figure 6B:
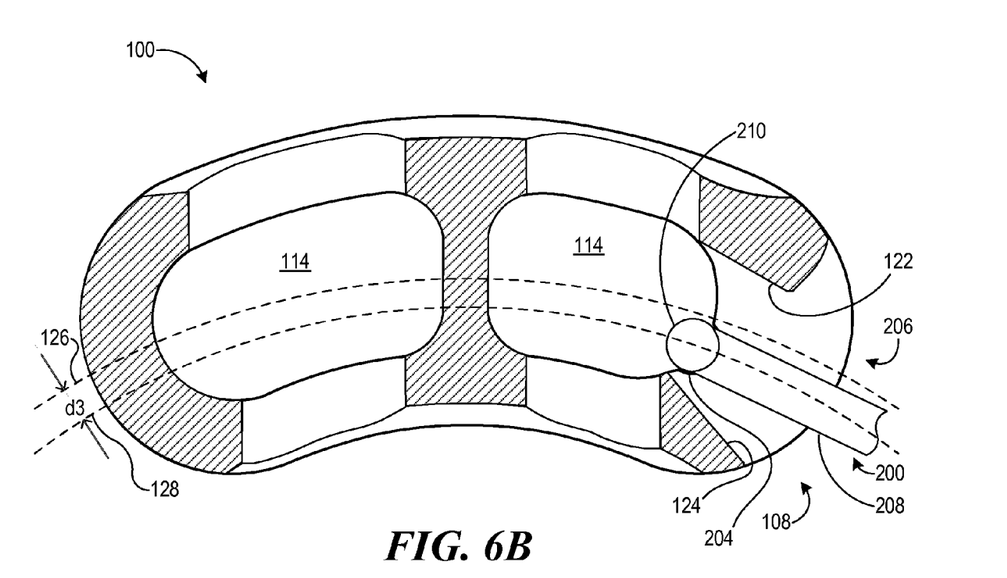
FIG. 6B illustrates a detailed cross-sectional view of the spacer of FIG. 2, as seem along line 6-6, and illustrating an insertion instrument in an engaged position.

Turning now to FIGS. 6A and 6B, further details of the spacer 100, an instrument 200, an insertion port 204 and the attachment slot 206, are illustrated. An interfacing portion of the insertion instrument 200 may comprise an appropriately shaped end, such as a t-bar for example, for securing the spacer 100 to the insertion instrument 200. In certain embodiments, the t-bar may have a longitudinal member coupled to a transverse member. The transverse member may be offset to either side of a midline of the longitudinal member to aid in release of the instrument 200 from the spacer 100. For example, the length of the transverse member on one side of the longitudinal member may be greater than the length of the transverse member on the opposite side of the longitudinal member. Of course, the shaped end may comprise many other equivalent configurations sufficient to secure the spacer 100 to the instrument 200. For example, the shaped end may comprise an overall "L" shape, with a cross-member having a rectangular or an oval cross-section. The shaped end of the insertion instrument 200 may comprise a shaft 208 and a cylindrical cross-member 210 extending beyond either side of the shaft 208.

FIG. 6A illustrates that the shaft 208 may be used to rotate the cross-member 210 about the shaft 208, so that the longitudinal axis of the cross-member 210 is approximately perpendicular to slot wall 122 and slot wall 124 of the attachment slot 206. Oriented in this manner, the cross-member 210 of the insertion instrument 200 may be inserted through the attachment slot 206 located in an lateral end 108 of the spacer 100. With the cross-member 210 inside of an internal cavity 114 of the spacer 100, the shaft 208 may then be used to re-orient the cross-member 210 so that a central axis of the cross-member 210 may be approximately parallel to the slot walls 122 and 124 of the attachment slot 206. In addition, the central axis of the cross-member 210 may also be substantially parallel to an axis defining the insertion port 204. As illustrated by FIG. 6B, by slightly translating the shaft 208 in a direction of withdrawal from the lateral end 108 of the spacer 100, the cross-member 210 may be seated in the insertion port 204. As a result, the cross-member 210 may rotatably engage the insertion port 204, thereby releasably securing the spacer 100 to the insertion instrument 200.

With the spacer 100 releasably secured to the instrument 200, the spacer 100 may then be inserted into the intervertebral space, positioned therein, and released or withdrawn using the insertion instrument 200. To release the spacer 100, the cross-member 210 may be slightly inserted into the internal cavity 114 and rotated to an orientation in which the central axis of the cross-member 210 may be substantially perpendicular to the slot walls 122 and 124 of the attachment slot 206. This released orientation of the cross-member 210 may be seen in FIG. 6A. To facilitate the withdrawal of the cross-member 210 from the attachment slot 206, the slot wall 122 and the slot wall 124 of the attachment slot 206 may respectively diverge toward the lateral end 108 of the spacer 100. Moreover, the diverging slot walls 122 and 124 may facilitate the removal of the cross-member 210 from the spacer 100 without regard to whether the spacer 100 may be in a rotated position or in a straight position (to be discussed later herein).

As seen in FIG. 6B, the insertion port 204 may be offset from a central radius of curvature 126 of the spacer 100. The offset may be determined between the central radius of curvature 126 of the spacer 100 and a concentric radius of curvature 128, which passes approximately through the axis defining the insertion port 204. The radial distance between the central radius of curvature 126 and the concentric radius of curvature 128 may be "d3."

Figure 7A:
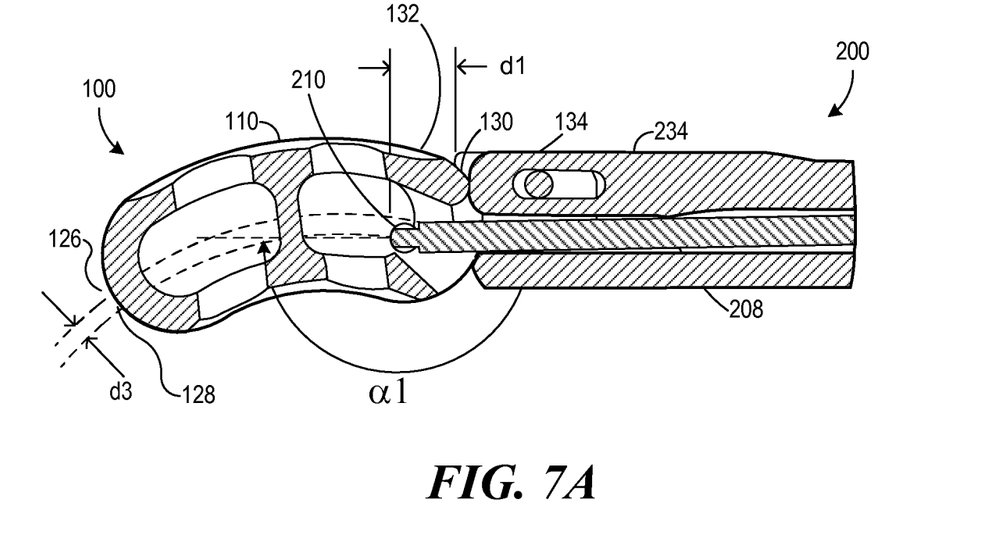
FIG. 7A illustrates a detailed cross-sectional view of a spacer coupled to an insertion instrument in a straight position.
Figure 7B:
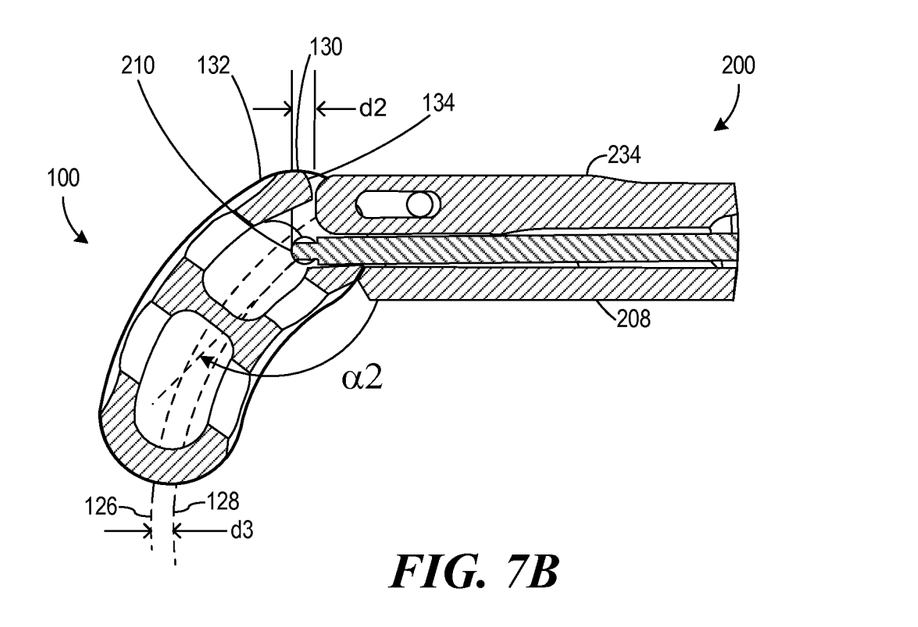
FIG. 7B illustrates a detailed cross-sectional view of the spacer and the insertion instrument of FIG. 7A in a rotated position.

Referring now to FIGS. 7A and 7B, the offset distance "d3" between the central radius of curvature 126 of the spacer 100 and the concentric radius of curvature 128 may facilitate the rotation of the spacer 100 relative to an insertion instrument 200 between a substantially straight position and a rotated position. The instrument 200 may comprise a pusher 234 for rotating the spacer 100. The pusher 234 may engage a side portion 130 of the outer radius of curvature 132 (i.e., the anterior side 110) of the spacer 100 and/or an abutment wall 134 that defines a widening portion of the attachment slot 206 (FIGS. 6A and 6B).

As shown by FIG. 7A, the pusher 234 may be located in a position in which the tip of the pusher 234 and the tip of the cross-member 210 are a distance "d1" apart. In this position, the spacer 100 may be in a substantially straight orientation defined by an angle "α1". Contrarily, with the pusher 234 located in a position illustrated by FIG. 7B, in which the tip of the pusher 234 and the tip of the cross-member 210 may be a distance "d2" apart, the spacer 100 may be in a rotated orientation defined by an angle "α2."

Moreover, in order to facilitate the rotation of the spacer 100, the offset "d3" of the insertion port 204 (and consequently the center of rotation of the spacer 100) may be located on a side of the central radius of curvature 126 opposite to the location of the side portion 130 and the abutment wall 134 at which the pusher 234 may engage the spacer 100. Accordingly, when the pusher 234 engages the abutment wall 134 with the spacer 100 in a substantially straight position relative to the insertion instrument 200, the spacer 100 rotates about a point on the concentric radius of curvature 128 (i.e., about the central axis of the cross-member 210 that is rotatably, releasably coupled to the insertion port 204).

Figure 8A:
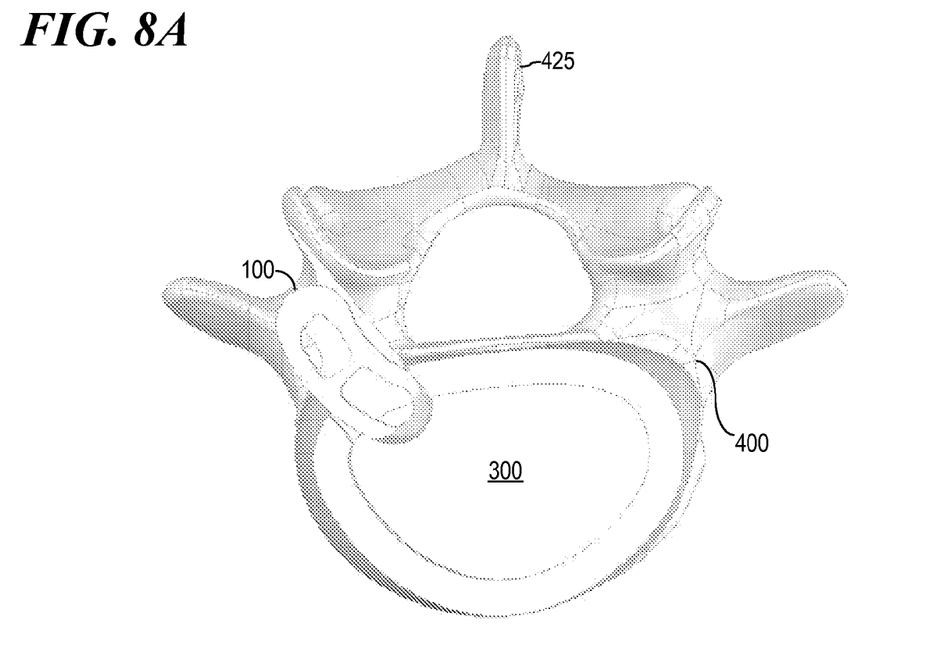
FIG. 8A illustrates a top view of the medial end of a spacer being inserted into an intervertebral space.
Figure 8B:
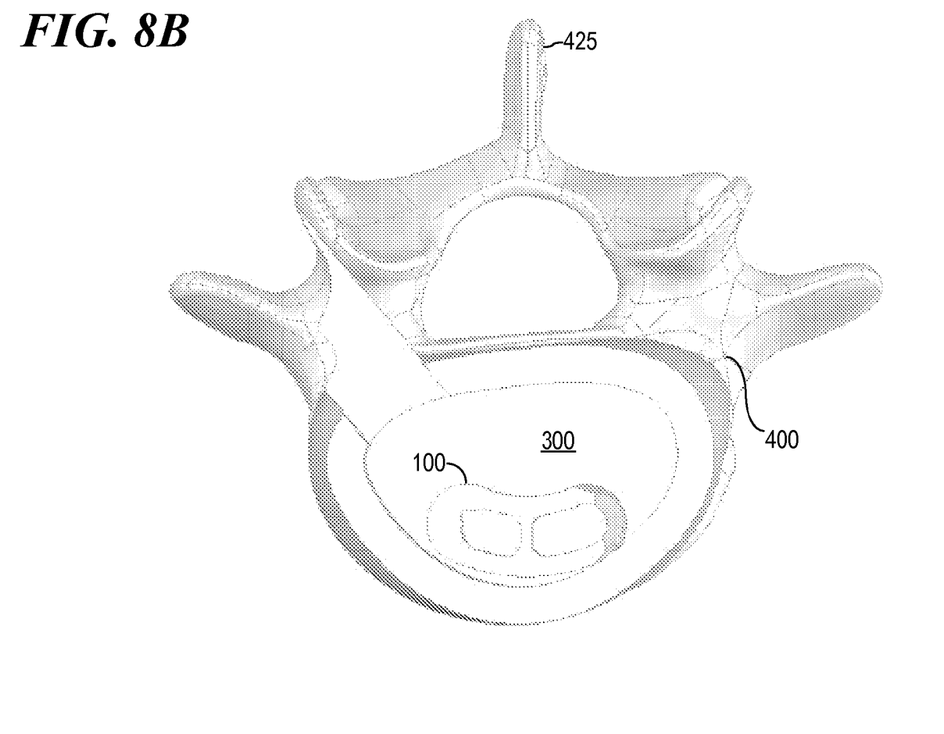
FIG. 8B illustrates a top view of the spacer of FIG. 8A fully inserted into the intervertebral space.

Referring now to FIGS. 8A and 8B, an illustrative embodiment of a spacer 100 may be inserted into the intervertebral disk space 300 from a posterior, lateral, or combination of posterior and lateral orientation (e.g., the posterior typically being divided into two quadrants on either side of the spine). Along the posterior of the vertebrae 400 is a spinous process 425. On a side of the vertebrae 400 opposing the spinous process 425 may be an anterior side. The spacer 100 may be inserted in a posterior lateral (shown in FIG. 8A), a posterior medial, or a direct posterior approach, among others. The medial end 106 (FIG. 4) of the spacer 100 may be initially inserted into the intervertebral space. As the spacer 100 is inserted, the spacer 100 may be rotated into a more appropriate orientation more proximate to the anterior side of the disk space 300 than the posterior side, as seen in FIG. 8B. Once the spacer 100 is inserted and the insertion instrument 200 (FIGS. 7A and 7B) is removed, the spacer 100 may be located through the use of one or more markers 119 (FIG. 4). As previously described, one marker 119 may be positioned at or near the attachment slot 206 (FIG. 5) of the lateral end 108 (FIG. 5). This marker 119 indicating the location of an attachment point of the spacer 100 may enable the surgeon or technician to reattach the insertion instrument 200 if the spacer 100 requires adjustment or removal.

The practice of using an embodiment of the present invention may facilitate the in vivo placement of spacers in the intervertebral space of a spine and in other cavities. Moreover, the use of an embodiment of the present invention may promote bone growth and result in more complete and effective fusion of adjacent vertebra. In addition, spacers constructed in accordance with certain embodiments may possess an improved ability to be retained in the intervertebral space. Further, the use of an embodiment of the present invention may operate to more readily restore the lordosis angle of a patient's spine.

It is understood that the present invention may take many forms and embodiments. Accordingly, several variations may be made in the foregoing without departing from the spirit or the scope of the invention. For example, an embodiment of the present invention may be practiced with a L-bar insertion instrument. The L-bar insertion instrument may comprise an L-shaped cross-member in place of the t-shaped cross-member of some of the illustrative embodiments. The L-shaped cross-member may enable minimally invasive insertion, placement, and release (or withdrawal) of spacers, particularly those spacers for use in the intervertebral spaces of a spine.

Having thus described the present invention by reference to certain exemplary embodiments, it is noted that the embodiments disclosed are illustrative rather than limiting in nature. A wide range of variations, modifications, changes, and substitutions are contemplated in the foregoing disclosure. In some instances, some features of an embodiment of the present invention may be employed without a corresponding use of other features. Many such variations and modifications may be considered obvious and desirable by those skilled in the art based upon a review of the foregoing description of illustrative embodiments. Accordingly, it is appropriate that the appended claims be construed broadly and in a manner consistent with the scope of the invention.

This invention claims:

1. A spinal implant for posterior or lateral placement between adjacent vertebrae, said implant comprising:
    a first dimension along a medial-lateral axis between a lateral end and a medial end of said implant;
    a second dimension along an anterior-posterior axis substantially orthogonal to said medial-lateral axis and less than said first dimension;
    a first bearing surface configured to abut a first vertebra;
    a second bearing surface configured to abut a second vertebra;
    a compound curve comprising a first radius in a first plane of curvature perpendicular to said anterior-posterior axis and a second radius in a second plane of curvature perpendicular to said medial-lateral axis, said second plane of curvature being orthogonal to said first plane of curvature and said compound curve defining at least one of said first bearing surface and said second bearing surface, said first radius in said first plane of curvature of said compound curve being longitudinally offset at a first non-zero distance along said medial-lateral axis from a longitudinal center axis of said implant;
    wherein said first radius is continuous from said lateral end to said medial end of said implant;
    a first cavity and a second cavity configured to extend through at least said first bearing surface and said second bearing surface; and
    an intermediate member interposed between said first cavity and said second cavity.

2. The spinal implant of claim 1 further comprising:
    a first end configured to be substantially semi-spheroidal in shape; and
    a second end configured to be substantially semi-circular when viewed perpendicular to one of said first and second bearing surfaces.

3. The spinal implant of claim 2 further comprising a first angled landing coupling one of said first and second bearing surfaces to said first end.

4. The spinal implant of claim 3 further comprising a second angled landing coupling said other of said first and second bearing surfaces to said first end.

5. The spinal implant of claim 1 further comprising at least one row of engaging protrusions configured to follow a contour of at least one of said first and second bearing surfaces.

6. The spinal implant of claim 5 wherein said at least one row of engaging protrusions comprises a first row of engaging protrusions and a second row of engaging protrusions configured to follow said contour of said first bearing surface and said second bearing surface.

7. The spinal implant of claim 1 further comprising a radiopaque marker member positioned proximate to an attachment slot of said implant.

8. The spinal implant of claim 1 wherein said second radius is in said second plane of curvature of said compound curve, said second radius being transversely offset at a second non-zero distance along said anterior-posterior axis from a transverse center axis of said implant.

9. A spinal implant for posterior or lateral placement between a first vertebral plate and a second vertebral plate of adjacent vertebrae, said implant comprising:
    an implant body wherein said implant body comprises:
        a length along a medial-lateral direction and a width along an anterior-posterior direction orthogonal to said medial-lateral direction, wherein said length being greater than said width of said implant body;
        a first bearing surface configured to abut the first vertebral plate,
        a second bearing surface configured to abut the second vertebral plate,
        said first bearing surface having a first curvature in said medial-lateral direction along said length of said body in a first plane of curvature defining a first radius about a first center of curvature, said first plane of curvature being perpendicular to said anterior-posterior direction, said first center of curvature being longitudinally offset at a first non-zero distance along said length away from a centroidal axis, wherein said first curvature extends in opposing directions from said first center of curvature in said medial-lateral direction along said length;
        said first bearing surface having a second curvature in said anterior-posterior direction along said width of said body in a second plane of curvature defining a second radius, said second plane of curvature being perpendicular to said medial-lateral direction;
        a first and second cavity open to at least said first bearing surface and said second bearing surface; and
        an intermediate member interposed between said first and said second cavity.

10. The spinal implant of claim 9 wherein said implant body comprises:
    a first end and a second end at opposing ends of said implant along said length;
    said first end comprises a first end thickness between said first bearing surface and said second bearing surface; and
    said second end opposite to said first end and that comprises a second end thickness between said first bearing surface and said second bearing surface not equal to said first end thickness.

11. The spinal implant of claim 10 wherein said implant body comprises:
    a third end and a fourth end at opposing ends of said implant along said width;
    said third end comprises a third end thickness between said first bearing surface and said second bearing surface; and
    said fourth end opposite to said third end and that comprises a fourth end thickness between said first bearing surface and said second bearing surface substantially equal to said third end thickness.

12. The spinal implant of claim 10 wherein said implant body comprises:
    a third end and a fourth end at opposing ends of said implant along said width;

said third end comprises a third end thickness between said first bearing surface and said second bearing surface; and said fourth end opposite to said third end and that comprises a fourth end thickness between said first bearing surface and said second bearing surface not equal to said third end thickness.

13. The spinal implant of claim 9 wherein said implant body comprises:
a first end and a second end at opposing ends of said implant along said width;
said first end comprises a first end thickness between said first bearing surface and said second bearing surface; and
said second end opposite to said first end and that comprises a second end thickness between said first bearing surface and said second bearing surface substantially equal to said first end thickness.

14. The spinal implant of claim 9 wherein said implant body comprises:
a first end and a second end at opposing ends of said implant along said width;
said first end comprises a first end thickness between said first bearing surface and said second bearing surface; and
said second end opposite to said first end and that comprises a second end thickness between said first bearing surface and said second bearing surface not equal to said first end thickness.

15. The spinal implant of claim 9 wherein:
said second radius in said second plane of curvature is defined about a second center of curvature, said second center of curvature being transversely offset at a second non-zero distance along said width away from said centroidal axis.

16. A spinal implant for placement within an intervertebral space between a first vertebra and an adjacent second vertebra, said implant comprising:
an implant body having a first cross-section in a medial-lateral direction along said implant, and further comprising:
a superior bearing surface configured to abut a first vertebra,
an inferior bearing surface configured to abut a second vertebra,
at least one of said superior bearing surface and said inferior bearing surface having a first curvature in said medial-lateral direction with a first radius about a first center of curvature, said first center of curvature being located in a first plane of curvature perpendicular to said medial-lateral direction, said first center of curvature being longitudinally offset at a non-zero distance along a length of said body away from a centroidal axis of said body in said first plane of curvature;
said implant having a second cross-section in an anterior-posterior direction along said implant substantially orthogonal to said medial-lateral direction, said implant body comprising:
at least one of said superior bearing surface and said inferior bearing surface having a second curvature in said anterior-posterior direction with a second radius;
a first cavity configured to establish a communicative pathway through said implant, between the first vertebra and the second vertebra;
a second cavity configured to establish a communicative pathway through said implant, between said first vertebra and the second vertebra;
an intermediate member between said first and said second cavity; and
an angled landing provided at the junction of said superior bearing surface or said inferior bearing surface and at one of opposing medial-lateral ends of said implant body.

17. The spinal implant of claim 16 further comprising a plurality of longitudinal radii in said medial-lateral direction.

18. The spinal implant of claim 16 further comprising a plurality of transverse radii in said anterior-posterior direction.

19. The spinal implant of claim 16 wherein said second radius is located in a second plane of curvature perpendicular to said anterior-posterior direction and is defined about a second center of curvature, said second center of curvature being transversely offset at a second non-zero distance along a width of said body away from said centroidal axis of said body in said second plane of curvature.

20. A spinal implant for placement within an intervertebral space between a first vertebra and an adjacent second vertebra, comprising:
an implant having a first end surface and a second end surface connected by first and second walls, and a first load bearing surface and a second load bearing surface;
said first load bearing surface having a first curvature in a medial-lateral direction along a length of said implant with a longitudinal radius about a center of curvature, said center of curvature being located in a first plane of curvature perpendicular to said medial-lateral direction, said implant having a centroidal axis centered on said length of said implant and said first plane of curvature, wherein said center of curvature of said longitudinal radius is longitudinally offset from said centroidal axis at a first non-zero distance along a direction of said length;
wherein said first curvature extends in opposing directions from said center of curvature of said longitudinal radius in said medial-lateral direction along said length of said implant; and
wherein said first load bearing surface having a second curvature in an anterior-posterior direction along a width orthogonal to said medial-lateral direction with a transverse radius about a second center of curvature, said second center of curvature being located in a second plane of curvature perpendicular to said anterior-posterior direction, said implant having said centroidal axis centered on said width of said implant and said second plane of curvature, wherein said second center of curvature of said transverse radius is transversely offset from said centroidal axis at a second non-zero distance along a direction of said width.

21. The spinal implant as in claim 20 wherein said first or said second load bearing surfaces include protrusions.

22. The spinal implant as in claim 20 wherein said implant includes one or more cavities therein.

23. The spinal implant as in claim 20 wherein said implant includes a plurality of said longitudinal radii.

24. The spinal implant as in claim 20 wherein said implant includes at least one local maximum height between said first load bearing surface and said second load bearing surface at said first non-zero distance in said medial-lateral direction.

* * * * *